United States Patent [19]

Noguchi

[11] Patent Number: 4,715,364

[45] Date of Patent: Dec. 29, 1987

[54] PELVIS LOCKING BELT

[76] Inventor: Katsumasa Noguchi, 42-13, Kabukicho 2 chome, Shinjuku-ku, Tokyo, Japan

[21] Appl. No.: 853,488

[22] Filed: Apr. 18, 1986

[30] Foreign Application Priority Data

Jun. 19, 1985 [JP] Japan .................................. 60-131946

[51] Int. Cl.$^4$ .............................................. A61F 5/24
[52] U.S. Cl. .................................. 128/96.1; 128/99.1; 128/69; 128/78; 2/311
[58] Field of Search ...................... 128/96, 98, 99, 100, 128/101, 102, 103, 104, 68, 69, 78, 538, 327, 168; 24/33; 2/311, 321, 322, 308

[56] References Cited

U.S. PATENT DOCUMENTS

| 26,756 | 4/1897 | Sanders | 128/DIG. 23 |
|---|---|---|---|
| 135,492 | 2/1873 | Ruediger | 24/33 B |
| 670,726 | 4/1901 | Pierce | 24/33 R |
| 1,924,640 | 8/1933 | Draves | 128/78 |
| 2,554,337 | 5/1951 | Lampert | 128/78 |
| 3,171,409 | 3/1965 | Cetrone | 128/99 |
| 3,920,008 | 11/1975 | Lehman | 128/96 |
| 4,576,154 | 3/1986 | Hyman et al. | 128/100 |

FOREIGN PATENT DOCUMENTS

| 3117090 | 12/1982 | Fed. Rep. of Germany | 128/68 |
|---|---|---|---|
| 131892 | 4/1951 | Sweden | 128/96 |

Primary Examiner—C. Fred Rosenbaum
Assistant Examiner—Ralph Lewis
Attorney, Agent, or Firm—Jordan and Hamburg

[57] ABSTRACT

A length-adjustable pelvis-locking belt which is tightly wound around portions immediately under the front upper spines of both iliums and a body side at the sacrum position. The belt comprises hard pressing mechanisms which are positioned at both parts corresponding to the spines and the femur trochanter major in the belt to inwardly press the body side between the spines and the femur trochanter major. The belt comprises a plurality of fastening belts which can be adjusted in length and connected to each other by means of connecting members. The pressing mechanism comprises a plurality of hard pressing members hinged foldably to each other.

7 Claims, 4 Drawing Figures

PELVIS LOCKING BELT

BACKGROUND OF THE INVENTION

1. Field of the Invention

The present invention relates to a pelvis locking belt, and more particularly to a pelvis locking belt which is tightly wound around the body in the periphery of the pelvis to lock the pelvis thereby correcting and stabilizing the loins, whereby the upper part of the body may be stabilized when a golf player swings a club or the like while impeding dissociation of the pelvis to prevent lumbago.

2. Description of the Prior Art

Where a person has to maintain his upright or seated attitude for a long period of time, for example, when a person drives a car for a long period of time in addition to the aforesaid swinging operation by a golf player, a load applied to the pelvis causes dissociation to occur in the ilium and sacrum which constitute the pelvis, often resulting in a lumbago.

In view of the foregoing, in a pelvis locking belt according to the present invention, the belt is tightly wound around the portions immediately under the front and upper spines of both iliums of the pelvis and the body side in the sacrum, and the pelvis and the femur trochanter major are locked together by means of a pressing mechanism to stabilize the loins and impede dissociation of the pelvis, thus preventing lumbago.

SUMMARY OF THE INVENTION

To achieve the aforementioned object, according to the present invention, there is provided a length-adjustable belt to be tightly wound around portions immediately under the front and upper spines of both iliums of the pelvis and the body side in the sacrum, wherein hard pressing mechanisms are provided at both parts between an ilium front spine and the femur trochanter major in the belt, the mechanisms inwardly urging the body side between the ilium front spine and the femur trochanter major with an inner curved surface corresponding to the body side.

More specifically, according to the above-described pelvis locking belt of the present invention, both pressing mechanisms are respectively positioned at the body side of the portions immediately under the front and upper spines of both iliums to make round the portions immediately under the front and upper spines of both iliums and the body side in the sacrum so as to tighten the pelvis. The aforesaid tightening causes the hard pressing mechanisms to suitably inwardly press the portions immediately under the front and upper spines of the ilium and both the femur trochanter major by pressure so as to share and carry the load applied to the pelvis from the side. Therefore, the dissociation of the pelvis is impeded to prevent occurrence of loins. Moreover, since the belt of the present invention will not restrict the movement of a joint as encountered in various gypsums, excellent wearing feeling is obtained.

DETAILED DESCRIPTION OF THE PREFERRED EMBODMENTS

Figure 1:
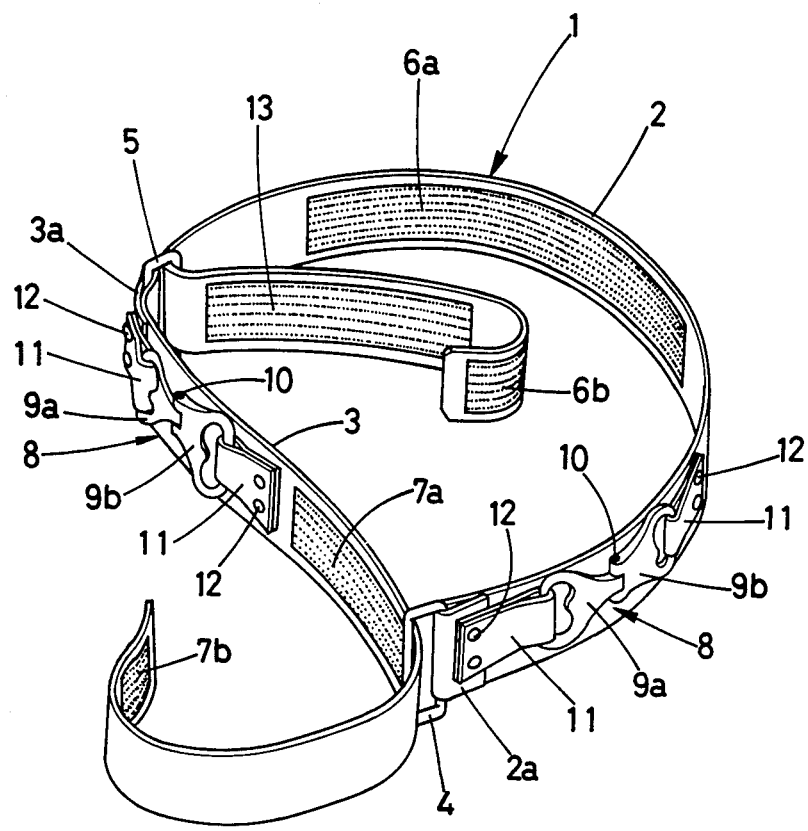
FIG. 1 is a perspective view showing a preferred embodiment of a pelvis locking belt in accordance with the present invention.
Figure 2:
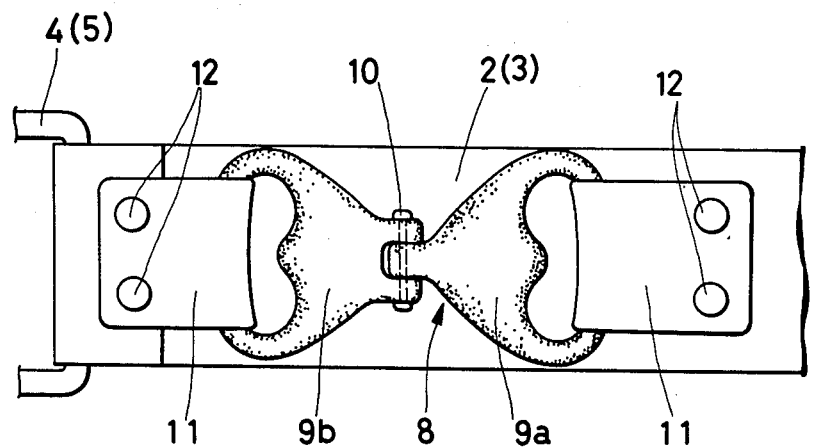
FIG. 2 is a front view showing essential parts thereof.
Figure 3:
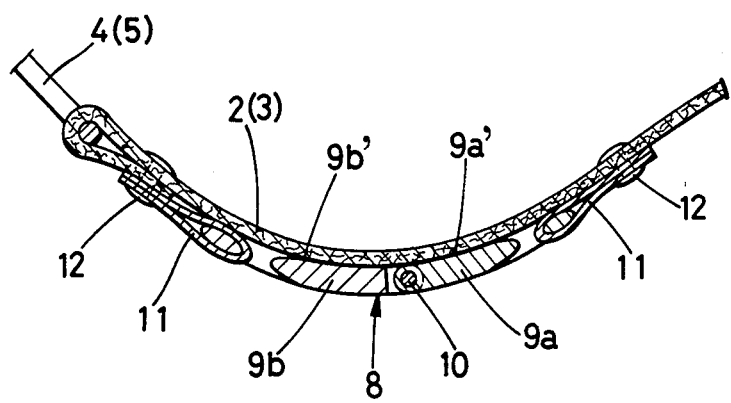
FIG. 3 is a cross-sectional view of essential parts.

Referring now to FIGS. 1 and 2, an annular belt 1, which is formed from a non-expansible flexible material such as natural leather or synthetic leather, has a back belt 2 and a front belt 3 which are connected to each other by means of annular connecting members 4, 5. More specifically, the connecting member 4 and connecting member 5 are mounted on an end 2a of the back belt 2 and an end 3a of the front belt 3, respectively. The back belt 2 is removably inserted into the connecting member 5 and inwardly folded back, and face fasteners 6a, 6b sewn to the inner surface of the back belt 2 are affixed to each other so that the back belt 2 may be connected to the front belt 3 adjustably in length, whereas the front belt 3 is removably inserted into the connecting member 4 and outwardly folded back. Face fasteners 7a, 7b sewn to the outer surface of the front belt 3 are affixed to each other so that the front belt 3 may be connected to the back belt 2 adjustably in length. A pressing mechanism 8 having two pressing members 9a, 9b, in the form of a metal cap opener bendably hinged to each other through a pin 10 is extended on the outer surface in the neighbourhood of the end 2a of the back belt 2 and on the outer surface in the neighborhood of the end 3a of the front belt 3 through small webs 11, 11 and riveted at 12. The pressing members 9a, 9b each have an inner surface formed with curved surfaces 9a', 9b' to correspond to the loins of the curved human body, as shown in FIG. 3. In FIG. 1, reference numeral 13 denotes an anti-deviation cloth sewn to the surface of the back belt 2 to assume the inside when the belt is worn to prevent the belt from being deviated when a user performs some action while wearing the pelvis locking belt.

Figure 4:
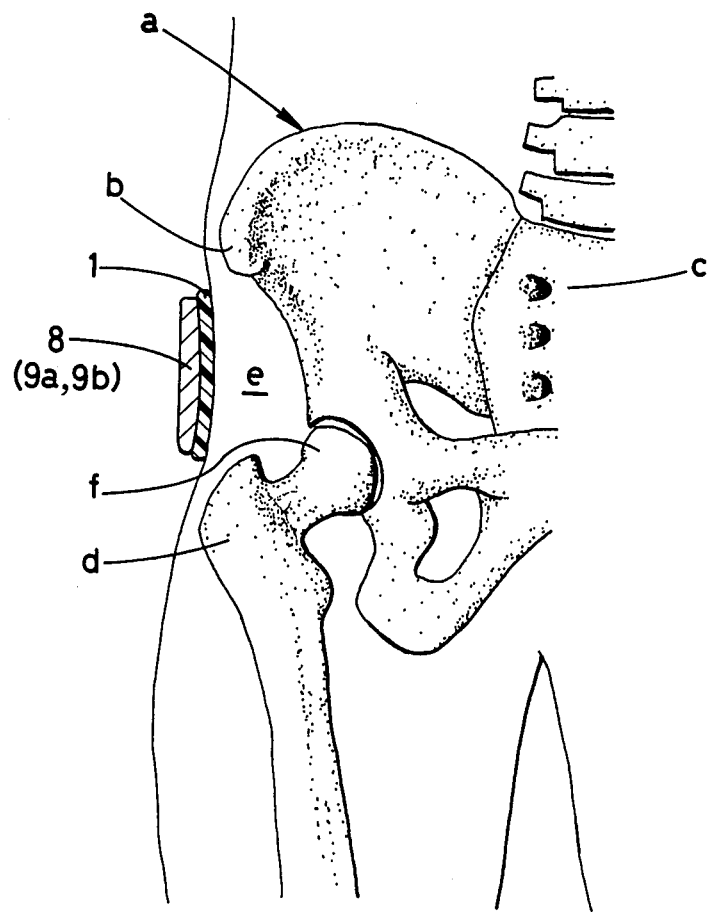
FIG. 4 is a view for explanation of the operation of the belt.

According to the pelvis locking belt constructed as described above, the length of the back belt 2 is adjusted in advance by the adjustment of the affixing position of the face fasteners 6a, 6b according to the loins and skeleton of the user, and both the pressing mechanisms 8, 8 are positioned at the body side of the portions immediately under the front upper spines b, b (only one of which is shown) of both iliums in the pelvis a as shown in FIG. 4 to make around of the portions b, b and the body side of the sacrum c to fasten and lock the pelvis a. The aforesaid fastening causes the metal-made hard pressing members 9a, 9b to assume the side position between the spine b and the femur trochanter major d to press the hypodermic layer e to lock the spine b and the femur trochanter major d. Accordingly, the load applied to the pelvis a is shared and carried from the side by both the pressing mechanisms 8, 8, that is, the load is carried not only by the femur head f but also by the femur trochanter major d. Therefore, for example, the unstable factor of the loins resulting from swinging operation of a golf club may be removed, and in addition, the pelvis a is firmly locked to prevent dissociation of the pelvis a resulting from the upright attitude and seated attitude for a long period of time, thus contributing to prevention of lumbago. Moreover, the pelvis locking belt is relatively narrow and will not restrict the movement of a joint as encountered in various medical gypsumes, and therefore, there involves no inconvenience in the driving of automobiles, swinging operation of a golf club and so on, providing excellent using feeling.

As described above, according to the pelvis locking belt of the present invention, the belt is tightly wound about the portions immediately under the front and upper spines of both iliums of the pelvis and the body side of the sacrum, and the aforesaid portions and the femur trochanter major are locked together from the side by means of the hard pressing mechanisms provided on the belt to impede dissociation of the pelvis due to the load. Thus, not only lumbago can be prevented but the load from the top is carried also from the side, and as a result, the stability of the loins may be improved and excellent using feeling may be obtained.

What is claimed is:

1. An adjustable pelvis locking belt comprising a front belt section of non-expandable material and a back belt section of non-expandable material, a first annular connecting member connected to a first end portion of said front belt section, a second annular connecting member connected to a first end portion of said back belt section, said front belt section having a second end portion which passes through said second annular connecting member and which folds back on itself to a position superimposed on a first part of said front belt section, first adjustable fastening means adjustably fastening said folded back second end portion of said front belt section and said first part of said front belt section, said back belt section having a second end portion which passes through said first annular connecting member and which folds back on itself to a position superimposed on a first part of said back belt section, second adjustable fastening means adjustably fastening said folded back second end portion of said back belt section and said first part of said back belt section, pressing means on each of said front and back belt sections, mounting means on each of said front and back belt sections mounting said pressing means on the outer side of the respective front and back belt sections, each of said pressing means comprising two metal pressing members, each of said pressing means further comprising pivotal means pivotably connecting each two metal pressing members, each of said pressing members having a curved inner surface corresponding to the curvature of the loins of a human body, whereby said first and second adjustable means are adjustable to position said pressing means in a position between the front upper spines of the ilium in the pelvis and the femur trochanter major to press the hypodermic layer therebetween to thereby lock said spines and said femur trochanter.

2. An adjustable pelvis locking belt according to claim 1 wherein each of said pressing members comprises a first and a second end part located on either side of an intermediate part, said first end part being in the form of a closed ring, said mounting means comprising webs passing through said closed ring, and fixing means fixing said web to the respective front or back belt section.

3. An adjustable pelvis locking belt according to claim 2 wherein said second end part has a transverse hole for receiving said pivotal means, said first end part being wider than said second end part, said intermediate part having a generally V-shaped configuration tapering down from said first to said second end part.

4. An adjustable pelvis locking belt according to claim 3 wherein said first and second end parts and said intermediate part have a continuous inside surface in contact with the outside of the respective front and back belt sections, said inside surface being curved to form said curved inner surface.

5. An adjustable pelvis locking belt according to claim 2 wherein said fixing means comprises rivets, and said webs pivotably mount said connecting members on the respective front and back belt sections.

6. An adjustable pelvis locking belt according to claim 3 wherein said pivotal means comprises a pin disposed in the aligned transverse hole of the pivotably connected pressing members.

7. An adjustable pelvis locking belt according to claim 6 wherein one pressing member of a pivotably connected pair has its second end part formed with a U-shaped configuration having two spaced legs and the other pressing member of said pivotably connected pair has its second end part disposed between said two spaced legs.

* * * * *